(12) United States Patent
Cho et al.

(10) Patent No.: US 9,777,297 B2
(45) Date of Patent: Oct. 3, 2017

(54) MICROBIAL PRODUCTION OF N-BUTYRALDEHYDE

(71) Applicants: Kwang Myung Cho, Los Angeles, CA (US); Wendy Higashide, Los Angeles, CA (US); Chrissie Lee, Long Beach, CA (US); Shahrooz Rabizadeh, Los Angeles, CA (US)

(72) Inventors: Kwang Myung Cho, Los Angeles, CA (US); Wendy Higashide, Los Angeles, CA (US); Chrissie Lee, Long Beach, CA (US); Shahrooz Rabizadeh, Los Angeles, CA (US)

(73) Assignee: EASEL BIOTECHNOLOGIES, LLC, Culver City, CA (US)

(*) Notice: Subject to any disclaimer, the term of this patent is extended or adjusted under 35 U.S.C. 154(b) by 18 days.

(21) Appl. No.: 14/356,386

(22) PCT Filed: Nov. 2, 2012

(86) PCT No.: PCT/US2012/063288
§ 371 (c)(1),
(2) Date: May 5, 2014

(87) PCT Pub. No.: WO2013/067325
PCT Pub. Date: May 10, 2013

(65) Prior Publication Data
US 2014/0322774 A1  Oct. 30, 2014

Related U.S. Application Data

(60) Provisional application No. 62/555,267, filed on Nov. 3, 2011.

(51) Int. Cl.
| | | |
|---|---|---|
| C12P 7/16 | (2006.01) | |
| C12P 7/24 | (2006.01) | |
| C12N 15/52 | (2006.01) | |
| C12N 1/21 | (2006.01) | |
| C12N 9/02 | (2006.01) | |
| C12N 9/04 | (2006.01) | |
| C12N 9/10 | (2006.01) | |

(52) U.S. Cl.
CPC ............ *C12P 7/16* (2013.01); *C12N 9/001* (2013.01); *C12N 9/0006* (2013.01); *C12N 9/0008* (2013.01); *C12N 9/1029* (2013.01); *C12N 15/52* (2013.01); *C12P 7/24* (2013.01); *C12Y 101/01157* (2013.01); *C12Y 102/01057* (2013.01); *C12Y 103/01086* (2013.01); *C12Y 203/01009* (2013.01)

(58) Field of Classification Search
None
See application file for complete search history.

(56) References Cited

U.S. PATENT DOCUMENTS

| 4,871,669 A * | 10/1989 | Murray ................. C12P 7/24 435/147 |
|---|---|---|
| 7,326,551 B2 | 2/2008 | Maupin-Furlow et al. |
| 7,358,404 B2 * | 4/2008 | Kawasaki et al. ............ 568/880 |
| 7,851,188 B2 | 12/2010 | Donaldson et al. |
| 7,993,889 B1 | 8/2011 | Donaldson et al. |
| 8,048,666 B1 | 11/2011 | Green et al. |
| 8,097,439 B2 | 1/2012 | Alibhai et al. |
| 8,188,250 B2 | 5/2012 | Bramucci et al. |
| 8,460,906 B2 * | 6/2013 | Contag ................. C12M 21/12 435/160 |
| 2009/0081746 A1 | 3/2009 | Liao et al. |
| 2009/0111154 A1 * | 4/2009 | Liao ..................... C12N 9/0006 435/160 |
| 2010/0003739 A1 | 1/2010 | Duhring et al. |
| 2010/0062505 A1 | 3/2010 | Gunawardena et al. |
| 2010/0209986 A1 | 8/2010 | Liao et al. |
| 2011/0008861 A1 | 1/2011 | Berry et al. |
| 2011/0020889 A1 | 1/2011 | Feldman et al. |
| 2011/0183392 A1 | 7/2011 | Feldman et al. |
| 2011/0201083 A1 | 8/2011 | Liao et al. |
| 2011/0250660 A1 | 10/2011 | Liao et al. |
| 2011/0281314 A1 | 11/2011 | Lynch |
| 2012/0028323 A1 | 2/2012 | Feldman et al. |
| 2012/0045809 A1 | 2/2012 | Buelter et al. |
| 2012/0064590 A1 | 3/2012 | Evanko et al. |
| 2012/0209021 A1 | 8/2012 | Kouba et al. |

FOREIGN PATENT DOCUMENTS

| EP | 2084287 B1 | 5/2012 |
|---|---|---|
| WO | 9406924 | 3/1994 |
| WO | 2009086423 A2 | 7/2009 |

(Continued)

OTHER PUBLICATIONS

U.S. Appl. No. 61/442,599, filed Feb. 24, 2011.*
Ezeji et al., Improving performance of a gas stripping-based recovery system to remove butanol from Clostridium beijerinckii fermentation, Bioprocess Biosyst. Eng., 2005, 27, 207-14.*
Wilkinson et al., Physical map of the Clostridium beijerinckii (formerly Clostridium acetobutylicum) NCIMB 8052 chromosome, J. Bacteriol., 1995, 177, 439-48.*
Uniprot, Accession No. P52643, 2010, www.uniprot.org.*
Groot et al., Batch and continuous butanol fermentations with free cells, Appl. Microbiol. Biotechnol., 1989, 32, 305-08.*
Zheng et al., Problems with microbial production of butanol, J. Ind. Microbiol. Biotechnol., 2009, 36, 1127-38.*
Baez, Antonino et al., High-flux isobutanol production using engineered *Escherichia coli*: a bioreactor study with in situ product removal, Appl Microbiol Biotechnol (2011) 90:1681-1690.

(Continued)

*Primary Examiner* — Robert Mondesi
*Assistant Examiner* — Todd M Epstein
(74) *Attorney, Agent, or Firm* — Lucas & Mercanti, LLP

(57) ABSTRACT

Microorganisms and methods of producing n-butyraldehyde with enhanced yields are presented in which a microorganism is engineered to enhance the conversion of a carbon source into n-butyraldehyde. The n-butyraldehyde is recovered by way of a gas stripping process that occurs during the conversion process, providing significantly greater product yield than post-fermentation recovery of n-butyraldehyde alone.

19 Claims, 6 Drawing Sheets

(56) References Cited

FOREIGN PATENT DOCUMENTS

| WO | 2009149240 A1 | 12/2009 |
| --- | --- | --- |
| WO | 2010062597 A1 | 6/2010 |
| WO | 2010075504 A2 | 7/2010 |
| WO | 2011005554 A2 | 1/2011 |
| WO | 2011057288 A2 | 5/2011 |
| WO | 2011128907 A1 | 10/2011 |
| WO | 2011140516 A2 | 11/2011 |
| WO | 2011159894 A1 | 12/2011 |
| WO | 2012004460 A2 | 1/2012 |
| WO | 2012045022 A2 | 4/2012 |
| WO | 2012061653 A2 | 5/2012 |
| WO | 2012061653 A9 | 5/2012 |
| WO | 20120999934 A2 | 7/2012 |
| WO | 2012109176 A2 | 8/2012 |
| WO | 2012125688 A2 | 9/2012 |

OTHER PUBLICATIONS

Ezeji, Thaddeus Chukwuekmeka et al., Bioproduction of butanol from biomass: from genes to bioreactors, Current Opinion in Biotechnology 2007, 18:220-227.

Rogers, Palmer et al., Clostridium acetobutylicum Mutants That Produce Butyraldehyde and Altered Quantities of Solvents, Appl. Environ. Microbiol. 1987, 53(12): 2761.

Shen, Claire R. et al., Driving Forces Enable High-Tier Anaerobic 1-Butanol Synthesis in *Escherichia coli*, Applied and Environmental Microbiology, May 2011, p. 2905-2915.

ISA/KR, International Search Report and Written Opinion, International Appln. No. PCT/US2012/063288, dated Mar. 28, 2013, 11 pages.

Shen, Claire R. et al., "Driving forces enable high-titer anaerobic 1-butanol synthesis in *Escherichia coli*," Applied and Environmental Microbiology, Mar. 11, 2011, vol. 77, No. 9, pp. 2905-2915, ISSN 0099-2240.

Rogers, Palmer et al.,"Clostridium acetobutylicum mutants that produce butyraldehyde and altered quantities of solvents," Applied and Environmental Microbiology, Dec. 1987, vol. 53, No. 12, pp. 2761-2766, ISSN 0099-2240.

Baez, Antonino, et al. "High-flux isobutanol production using engineered *Escherichia coli*: a bioreactor study with in situ product removal," Applied and Environmental Microbiology, Mar. 19, 2011, vol. 90, No. 5, pp. 1681-1690, ISSN 0175-7598.

Ezeji, Thaddeus Chukwuemeka, et al., "Bioproduction of butanol from biomass: from genes to bioreactors," Current Opinion in Biotechnology, Apr. 25, 2007, vol. 18, No. 3, pp. 220-227, ISSN 0958-1669.

\* cited by examiner

MICROBIAL PRODUCTION OF N-BUTYRALDEHYDE

This application claims priority to our U.S. provisional application with the Ser. No. 61/555,267, which was filed Nov. 3, 2011.

FIELD OF THE INVENTION

The field of the invention is production of fine chemicals, and especially microbial production of n-butyraldehyde.

BACKGROUND OF THE INVENTION

Over 10 million metric tons of oxo-chemicals are consumed annually for the synthesis of a wide array of industrial and consumer products, including plasticizers, antifreeze products, aircraft and runway de-icing products, solvents, hydraulic fluids, paints, lubricants, cosmetics, fine chemicals, and pharmaceuticals. Currently, the dominant technology for $C_3$-$C_{15}$ oxo-chemical production is hydroformylation, also known as oxo-synthesis or the oxo-process. This catalytic chemical process involves the addition of a formyl group and a hydrogen atom to an olefin (a hydrocarbon with a carbon-carbon double bond) under high temperature and pressure conditions. Propylene-derived $C_4$ oxo-chemicals account for nearly 73% of the worldwide consumption of oxo-chemicals. The production of $C_4$ oxo-chemicals requires propylene as starting material, making the process not sustainable. The substantial energy costs for maintaining the high temperature and pressure conditions necessary in the current manufacturing process limits the overall energy efficiency and is thus deemed environmentally unfriendly.

Therefore, new methods for producing $C_4$ oxo-chemicals using biological conversion of renewable resources such as sugar and cellulose have been developed and more recently also deployed. Among other advantages, it should be noted that biomass-derived substrates fix $CO_2$ naturally, leading to a carbon neutral oxo-chemical production process.

Another approach to producing oxo-chemicals involves the metabolic engineering of microorganisms to produce chemicals of interest. For example, various *Clostridium* species (without genetic alteration) may be cultured to produce 1-butanol. However, all or almost all of those known processes require separation of the 1-butanol and so have high recovery cost. Selected strains of *Clostridium* have been metabolically engineered to enhance the expression of 1-butanol over other products, however the lack of genetic tools available for regulating the metabolic pathways of *Clostridium* has impeded progress in that avenue. To circumvent the difficulties associated with metabolic engineering of *Clostridium*, various alternative microbial species have been considered that are better understood and more easily modified, including *Escherichia coli* and *Saccharomyces cerevisiae*, among others.

Notwithstanding the difficulties with *Clostridium*, Kouba et al. teach in U.S. Pat. App. No. 2012/0209021, incorporated herein by reference in its entirety, a method of producing n-butyraldehyde using recombinant solventogenic bacteria and recombinant microorganisms. Here, Kouba et al. describe a two-step method involving recombinant *Clostridium* in which (1) the recombinant bacterium is cultured and (2) the resulting n-butyraldehyde is isolated from the culture medium upon termination of fermentation. While such approach is at least conceptually desirable, several drawbacks nevertheless remain. Among other things, the yield of n-butyraldehyde in the system of Kouba is relatively low.

Thus, even though various systems and methods of production of n-butyraldehyde are known in the art, all or almost all of them suffer from one or more drawbacks. Consequently, there is still a need to provide improved systems and methods for microbial production of n-butyraldehyde.

SUMMARY OF THE INVENTION

The inventive subject matter is drawn to microorganisms, methods, and systems in which a microorganism is genetically engineered to produce n-butyraldehyde. Most preferably, such production is based on improved molar yield of acetyl-CoA from metabolic conversion of various saccharides, and especially glucose. So produced acetyl-CoA is then condensed using a sequence of (preferably recombinant) enzymes, and the condensation product is subsequently reduced over multiple steps to n-butyraldehyde. It is still further preferred that one or more microbial alcohol dehydrogenases are reduced or eliminated to prevent further degradation of n-butyraldehyde.

In further particularly preferred aspects, the produced n-butyraldehyde is removed by a sparging process while the microorganism is cultured to achieve (a) heretofore unknown cumulative yields of n-butyraldehyde, (b) an $MCY_{50}$ of 24 hours or less, (c) a dissolved n-butyraldehyde concentration of 1.0 g/L or less, and/or (d) a net increase in cell density over at least 24 hours.

In one especially preferred aspect, a method of producing n-butyraldehyde includes a step of culturing a microorganism (e.g., genus preferably *Escherichia* (and particularly *E. coli*), *Corynebacterium*, *Clostridium*, *Zymonomas*, *Salmonella*, *Rhodococcus*, *Pseudomonas*, *Bacillus*, *Lactobacillus*, *Enterococcus*, *Alcaligenes*, *Klesiella*, *Paenibacillus*, *Arthrobacter*, *Brevibacterium*, *Pichia*, *Candida*, *Hansenula*, *Synechococcus*, *Synechocystis*, *Anabaena*, *Ralstonia*, *Lactococcus*, or *Saccharomyces*) in a culture medium with a carbon source, wherein the microorganism is engineered to express at least one heterologous gene and by deletion of at least one native gene to so allow for conversion of the carbon source into n-butyraldehyde. In another step, the produced n-butyraldehyde is recovered from the culture medium by a gas stripping process to a cumulative yield of n-butyraldehyde of at least 1.5 g/L, wherein the recovering step is performed during the culturing step.

Most preferably, the heterologous gene is an acetyl-CoA acetyltransferase, a 3-hydroxyacyl-CoA dehydrogenase, a crotonyl-CoA hydratase, a butyryl-CoA dehydrogenase, a trans-enoyl-CoA reductase, and/or a butanal dehydrogenase, or the microorganism is genetically modified to express an artificial operon to allow for expression of atoB, crt, hbd, and bldh. It is further generally preferred that the microorganism is genetically modified to have reduced or abolished expression of ldhA, adhE, frdBC, pta, and/or yqhD.

While not limiting to the inventive subject matter, the gas stripping process uses sparging with a stripping gas at a sparging rate of at least 1 vessel volume per minute, wherein the culture time is 24 hours or less. It is still further preferred that the recovering step is performed to a cumulative yield of 2.0 g/L at or before 40 hours of culture time. Additionally, it is contemplated that the n-butyraldehyde can be reduced to n-butanol in vapor phase, or that the n-butyraldehyde is condensed from the stripping gas and reduced to n-butanol in liquid phase.

Viewed from one perspective, the inventors also contemplate a method of producing n-butyraldehyde in which a microorganism is cultured in a culture medium with a carbon source, wherein the microorganism is engineered to express at least one heterologous gene and by deletion of at least one native gene to so allow for conversion of the carbon source into n-butyraldehyde. In another step, the produced n-butyraldehyde is recovered from the culture medium by a gas stripping process that comprises a step of sparging under conditions effective to provide 50% of a maximum cumulative yield ($MCY_{50}$) at or before 24 hours culture time, wherein the recovering step is performed during the culturing step. Most preferably, the culturing step is a batch culture over at least 18 hours, and the $MCY_{50}$ is recovered in 20 hours or less (e.g., wherein the $MCY_{50}$ is at least 1 g/L).

Viewed from another perspective, the inventors also contemplate a method of producing n-butyraldehyde in which a microorganism is cultured in a culture medium with a carbon source, wherein the microorganism is engineered to express at least one heterologous gene and by deletion of at least one native gene to so allow for conversion of the carbon source into n-butyraldehyde. In a further step, the produced n-butyraldehyde is recovered from the culture medium by a gas stripping process (e.g., using continuous sparging) at a sparging rate effective to maintain dissolved n-butyraldehyde at a concentration below a viability threshold concentration, wherein the recovering step is performed during the culturing step. As before, it is generally preferred that the (continuous) sparging is at a sparging rate of at least 1 vessel volume per minute, and/or that the dissolved n-butyraldehyde concentration is maintained at or below 1.0 g/L.

Therefore, the inventors also contemplate a method of producing n-butyraldehyde that includes a step of culturing a microorganism with a carbon source, wherein the microorganism is engineered to express at least one heterologous gene and by deletion of at least one native gene to so allow for conversion of the carbon source into n-butyraldehyde. In a further step, the produced n-butyraldehyde is recovered from the culture broth by a gas stripping process at a sparging rate effective to prevent a net decline of cell density for up to at least 40 hours, wherein the recovering step is performed during the culturing step. Most preferably, the sparging rate is effective to produce a net increase in cell density over at least 24 hours.

Various objects, features, aspects and advantages of the inventive subject matter will become more apparent from the following detailed description of preferred embodiments, along with the accompanying drawing figures in which like numerals represent like components.

DETAILED DESCRIPTION

The inventors have now discovered that enhanced yields of n-butyraldehyde may be obtained by creating or culturing an engineered microorganism to produce n-butyraldehyde from various carbon sources while sparging the fermentor with a (preferably inert gas) during the fermentation reaction.

It should be appreciated that in this manner the product is not allowed to accumulate and subsequently collected at the end of the process. Instead, sparging during fermentation is used to drive off n-butyraldehyde, which unexpectedly appeared to increase production rate, prolong the viability, and/or production life of the engineered microorganisms. Consequently, significantly higher cumulative yields are achieved than with accumulation of the product in the fermentation medium. Sparging during fermentation may be continuous or discontinuous, at variable or constant rates, at any reasonable combination thereof.

Once driven off the fermentation medium, various methods may be used to recover the n-butyraldehyde, including trapping in solution, by dissolution or adsorption into solvent, or via adsorption onto a solid sorbent. The so recovered product may then be sold as a commodity or converted to a desirable product via oxidation, reduction, or condensation.

It should further be appreciated that the engineered microorganism may be made from a variety of microorganisms that are modified to produce n-butyraldehyde, including various bacteria, cyanobacteria, and fungi. Preferred engineered microorganisms have also been modified to inhibit downstream reactions using n-butyraldehyde as a reagent, thereby further enhancing yield of the n-butyraldehyde product. Appropriate carbon sources include various proteins, carbohydrates, and lipids (all pure or mixtures), and any synthetic or man-made mixtures thereof (e.g., cell extracts, biomass, biosolids, etc.).

Figure 1:
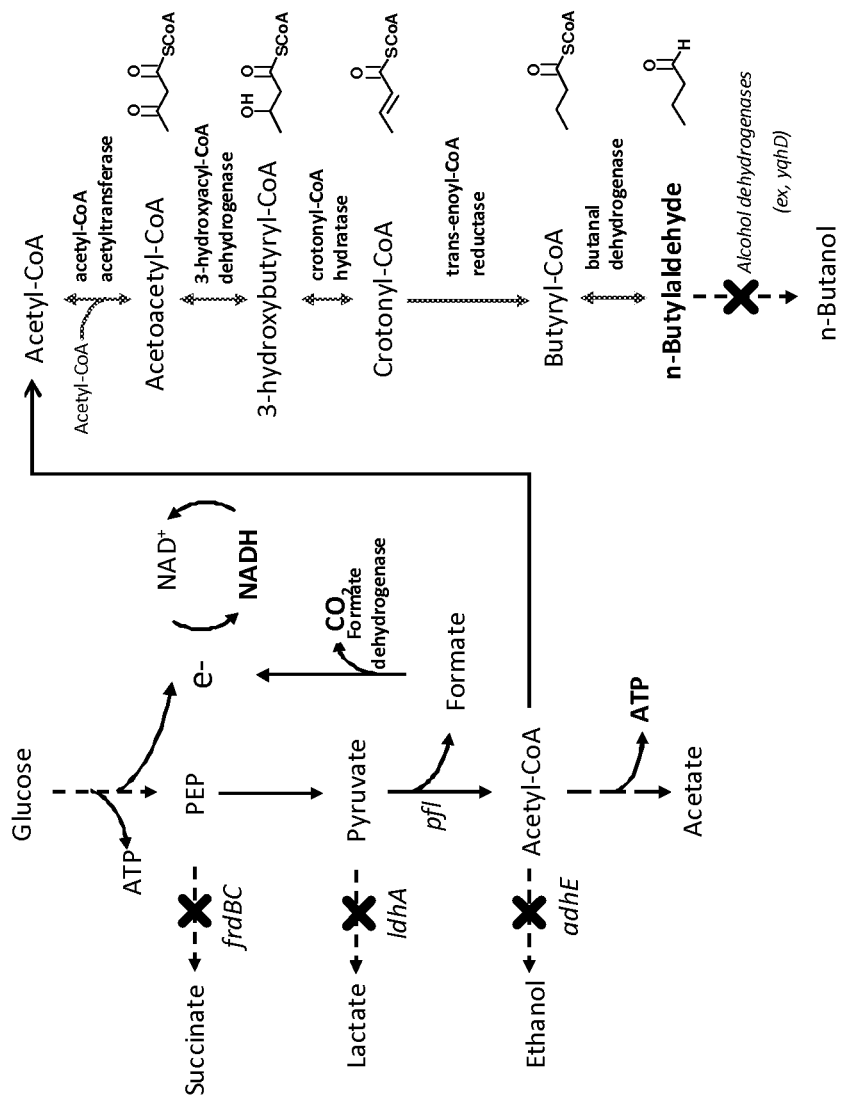
FIG. 1 is a schematic representation of an exemplary engineered metabolic pathway for conversion of glucose to n-butyraldehyde.

In view of the foregoing, and in one preferred aspect of the inventive subject matter, it is generally contemplated that a recombinant microorganism, and especially E. coli expresses a group of genes to so enable production of n-butyraldehyde. Most typically, recombinant expression includes expression of at least one gene encoding a polypeptide having acetyl-CoA acetyltransferase activity, expression of at least one gene encoding a polypeptide having hydroxybutyryl-CoA dehydrogenase activity, expression of at least one gene encoding a polypeptide having crotonyl-CoA hydratase activity, expression of at least one gene encoding a polypeptide having trans-enoyl-CoA reductase activity, and/or expression of at least one gene encoding a polypeptide having butanal dehydrogenase activity. FIG. 1 illustrates an exemplary engineered metabolic pathway.

Consequently, it should be appreciated that an engineered microbial cell will comprise any combination of native and heterologous enzymes needed to produce n-butyraldehyde. For example, the cell may comprise a native or heterologous acetyl-CoA acetyltransferase enzyme, a native or heterologous hydroxybutyryl-CoA dehydrogenase, a native or heterologous crotonyl-CoA hydratase, a native or heterologous trans-enoyl-CoA reductase, and/or a native or heterologous butyraldehyde dehydrogenase. More specifically, the acetyl-CoA acetyltransferase can be any enzyme capable of catalyzing the conversion of acetyl-CoA to acetoacetyl-CoA. In some embodiments, the acetyl-CoA acetyltransferase has an E.C. number of 2.3.1.9. One gene encoding an exemplary acetyl-CoA acetyltransferase is *Escherichia coli* atoB (GenBank Nos: NP_416728.1. NC_000913.2). Likewise, the 3-hydroxybutyryl-CoA dehydrogenase can be any enzyme capable of catalyzing the conversion of acetoacetyl-CoA to 3-hydroxybutyryl-CoA. In some embodiments, the 3-hydroxybutyryl-CoA dehydrogenase has an E.C. number of 1.1.1.157. A 3-hydroxybutyryl-CoA dehydrogenase is *Clostridium acetobutylicum* hbd (GenBank No: NP_349314.1. NC_003030.1). The crotonyl-CoA hydratase can be any enzyme capable of catalyzing the conversion of 3-hydroxybutyryl-CoA to crotonyl-CoA. In some embodiments, the crotonyl-CoA hydratase has an E.C. number of 4.2.1.55. An exemplary crotonyl-CoA hydratase is *Clostridium acetobutylicum* crt (GenBank Nos: NP_349318.1. NC_003030.1). The trans-enoyl-CoA reductase can be any enzyme capable of catalyzing the conversion of crotonyl-CoA to butyryl-CoA. In some embodiments, the trans-enoyl-CoA reductase has an E.C. number of 1.3.1.38. An exemplary trans-enoyl-CoA reductase is *Treponema denticola* ter (GenBank Nos: NP_971211 NC_002967.9). The butanal dehydrogenase can be any enzyme capable of catalyzing the conversion of butyryl-CoA to butyraldehyde. In some embodiments, the butanal dehydrogenase has an E.C. number of 1.2.1.57. An exemplary butanal dehydrogenase is *Clostridium saccharoperbutylacetonicum* NI-4 bldh.

In other preferred embodiments, it should be appreciated that genes that do not directly participate in the production of n-butyraldehyde may be expressed to increase n-butyraldehyde production/titer to so achieve a favorable balance in an equilibrium reaction. For example, the cell may comprise a native or heterologous formate dehydrogenase to provide a metabolic driving force for the production pathway to n-butyraldehyde. The production and subsequent loss of $CO_2$ prevents the reversible reaction. The formate dehydrogenase can be any enzyme capable of catalyzing the conversion of formate to $CO_2$. In some embodiments, the formate dehydrogenase has an E.C. number of 1.2.1.2. One gene encoding an exemplary formate dehydrogenase is *Candida boidinii* fdh (GenBank Nos: AF004096, AJ245934, AJ011046, DQ458777). Further suitable modifications and cell lines are described in WO 2012/125688A2, EP2084287B1, US8188250B2, US20110281314A1, US20120064590A1, WO2012004460A2, WO2012045022A2, WO2012061653A2, WO2012061653A9, WO2012099934A2, WO2012109176A2, and WO2012125688A2, all of which are incorporated by reference herein.

Consequently, it should be noted that the alcohol production in contemplated cells will be significantly reduced as compared to unmodified corresponding cells. Preferably, the alcohol production is reduced by about 10%, 20%, 30%, 40%, 50%, 60%, 70%, 80%, 90%, 95%, or more than about 95% by mass or volume as compared to that produced in an unmodified control cell. More preferably, alcohol production is reduced by about 99%, and most preferably, the contemplated recombinant host cells produce no detectable alcohol. In some embodiments, one or more alcohol dehydrogenase genes are knocked out or otherwise disabled. More preferably, all alcohol dehydrogenase genes are knocked out or otherwise disabled.

With respect to the microbial cell it should be appreciated that the particular organism is not critical to the inventive subject matter so long as such microorganism is capable of recombinant modification and production of n-butyraldehyde. Therefore, suitable organisms include various bacteria, cyanobacteria, or fungi. For example, the microorganism in some embodiments may belong to a genus selected from the group consisting of *Escherichia, Bacillus, Corynebacterium, Alcaligenus, Zymomonas, Clostridium, Lactobacillus, Synechococcus, Synechocystis, Saccharomyces, Pichia, Candida, Hansenula*, and *Aspergillus*. In particularly preferred embodiments, the microorganism is *Escherichia coli, Bacillus subtilis, Synechococcus elongatus, Ralstonia eutropha*, or *Saccharomyces cerevisiae*.

The recombinant microorganism may be prepared using any method known to one of ordinary skill in the art, and it will be understood that modifications may include insertion or deletion of one or more genes as deemed necessary to increase or decrease activity of a particular enzymatic pathway. In some embodiments, a mutant microorganism may also be used in the methods of the present invention, and may be further modified recombinant as desired. Thus, suitable modifications will include random mutagenesis to produce deficient expression patterns, extrachromosomal (typically plasmids or phagemid) nucleic acids with suitable control elements to produce controlled overexpression of one or more enzymes, genomic insertions with suitable control elements to produce controlled overexpression of one or more enzymes, etc.

With regard to actual production of n-butyraldehyde it is therefore contemplated that suitable methods include fermenting an engineered microorganism as described herein under conditions that allow the microorganism to use a carbon source to thereby produce n-butyraldehyde. The so produced n-butyraldehyde is contemporaneously recovered and purified using well known gas stripping methods (e.g., sparging an inert gas through the culture medium), and subsequently purified using well known methods (e.g., condensation). Most typically, the concentration [gram/liter] of n-butyraldehyde produced in the microorganism is substantially greater than the concentration [gram/liter] of alcohol produced in the microorganism. For example, the ratio of the concentration of n-butyraldehyde as compared to the concentration of alcohol is at least 80:20. More preferably, the ratio is 90:10, 95:5, or 99:1.

The carbon source may be any suitable carbon source appropriate to the selected microorganism, such as glucose, fructose, sucrose, starch, cellulose, hemicelluloses, glycerol, carbon dioxide, protein, and/or amino acids. Any combination of the foregoing and/or other suitable carbon source may also be used. The person of ordinary skill in the art will be readily able to select the appropriate carbon source based on the type of microbial organism selected. However, particularly preferred carbon sources include those that are carbon-neutral. Thus, and among other suitable choices, carbon sources will include various hydrolysates (hemicellulosic, proteinaceous, etc) and raw sugars.

EXAMPLES

The following example demonstrates production of n-butyraldehyde from glucose by an engineered *E. coli* strain which has the ldhA, adhE, frdBC, and yqhD genes knocked out, but containing atoB-hbd-crt-ter-bldh-fdh genes. The so engineered host strain for n-butyraldehyde production, *E. coli* strain EB10, is an *E. coli* BW25113 (rrnBT14 ΔlacZWJ16 hsdR514 ΔaraBADAH33 ΔrhaBADLD78)

derivative with F' transduced from XL-1 blue to supply lacIq and gene knockouts in the ldhA, adhE, frdBC, and yqhD genes. The strain was further optimized with an additional pta deletion in EB 10, resulting in EB 12.

Thus, the strains can be characterized as follows: EB10: BW25113 with knock-outs in ldhA, adhE, frdBC, and yqhD. EB11: BW25113 with knock-outs in: ldhA, adhE, frdBC, and yqhD (pEB73, pIM8, pCS138). EB12: BW25113 with knock-outs in: ldhA, adhE, frdBC, yqhD AND pta. EB13: BW25113 with knock-outs in: ldhA, adhE, frdBC, yqhD AND pta (pEB73, pIM8, pCS138).

For this particular example, three plasmids were constructed and used for n-butyraldehyde production. The first plasmid has an artificial operon constructed for the overexpression of the atoB-crt-hbd-bldh genes with $\lambda P_L$ promoter and lac operator sequence. The second plasmid has a ter gene with $\lambda P_L$ promoter and lac operator sequence. The third plasmid has fdh gene with $\lambda P_L$ promoter and lac operator sequence. EB10 and EB12 cells are transformed to contain all three plasmids to form EB11 and EB13, respectively. The resulting engineered n-butyraldehyde production strain was named as E. coli EB11 and EB13, respectively. E. coli strain EB10 and EB11 were pre-cultured in test tubes containing 3 ml of LB medium at 37° C. overnight on a rotary shaker (250 r.p.m.) with ampicillin (100 μg/ml), kanamycin (50 μg/ml), and chloramphenicol (25 μg/ml), where necessary. Overnight cultures were diluted 1:100 into 5 ml of fresh medium with the same antibiotics. The fresh medium is terrific broth (TB) (12 g tryptone, 24 g yeast extract, 2.31 g $KH_2PO_4$, 12.54 g $K_2HPO_4$, 4 ml glycerol per liter of water) supplemented with 2% glucose. Cells were grown to an $OD_{600}$ of 0.4 to 0.6 and then induced with 0.1 mM isopropyl-β-D-thiogalactoside (IPTG) for another 1 to 2 h aerobically at 37° C. overnight on a rotary shaker (250 r.p.m.). The cultures were transferred from the test tubes to 10-ml BD Vacutainer sealed tubes. Oxygen was evacuated and replaced with $N_2$ gas. Fermentation was allowed to proceed for 24 hours at 37° C. overnight on a rotary shaker (250 r.p.m.).

Bioreactor production of n-butyraldehyde: Strain EB12 was used in the fermentation for bioreactor production of n-butyraldehyde. The overnight preculture was inoculated in LB containing the appropriate antibiotics and allowed to grow at 37° C. in a rotary shaker at 250 rpm. N-butyraldehyde fermentation was performed in a 5-liter stirred-tank bioreactor (Eppendorf, Hauppauge, N.Y., USA), using a working volume of 2.0 liters. The bioreactor was inoculated with 23 mls of overnight preculture, and 0.1 mM IPTG was added at the time of inoculation to induce the expression of the enzymes involved in the n-butyraldehyde production pathway. Dissolved oxygen (DO) during the aerobic stage was maintained at 20% with respect to air saturation by raising the stirrer speed (from 200 rpm to 500 rpm). The cells were grown at 30° C. under aerobic conditions in batch mode until the optical density reached approximately $OD_{600}=0.8$. Then, the agitation was set to 350 rpm and the specified vvm (volume of gas per volume of liquid per minute) of nitrogen was bubbled through the bioreactor with two goals: (i) to switch to anaerobic conditions and (ii) to accomplish in situ gas stripping of n-butyraldehyde. Upon the anaerobic switch, intermittent linear feeding of glucose solution (500 g/liter) was initiated to maintain a glucose concentration between 10 and 20 g/L. The evaporated n-butyraldehyde was condensed using a Graham condenser and then passed through a series of three traps filled with water (4° C.). The pH was controlled at 6.8 at all times by the automatic addition of 5M NaOH solution. At the specified time points, fermentation samples were collected to determine cell growth, n-butyraldehyde production, and glucose concentration and the water in the traps were replaced. Alcohol compounds produced by the analyzed strains were identified by GC-MS. The system included a model 6890N network GC system (Agilent Technologies), a model 7883B injector and autosampler (Agilent Technologies) and a model 5973 network mass selective detector (Agilent Technologies). A DB-5 ms capillary column (30 m, 0.25-mm internal diameter, 0.25-μm film thickness; Agilent Technologies) was used, with helium (1 ml/min$^{-1}$) as the carrier gas. An oven temperature is programmed from 75° C. (2.6 min) to 200° C. at 30° C./min$^{-1}$. The injector and detector are maintained at 250° C. Alcohol compounds are isolated by solvent extraction. Three-hundred microliters of supernatant of culture broth are extracted after centrifugation with 150 μl GC standard grade toluene (Fluka). A 1 μl sample is injected in split injection mode with a 30:1 split ratio.

Figure 2A:
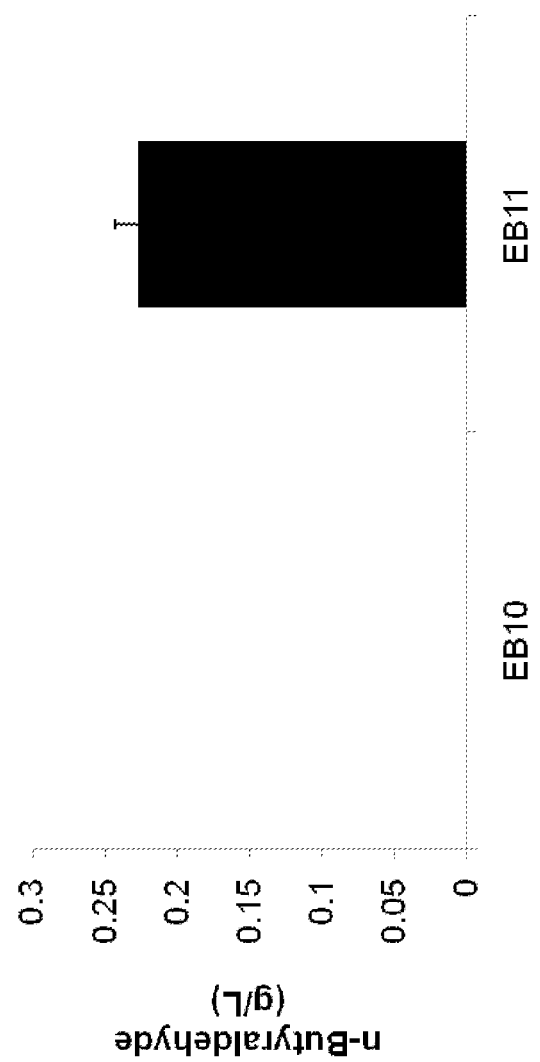
FIG. 2A is an exemplary bar graph depicting results of n-butyraldehyde production (g/L) from glucose by metabolically engineered E. coli strain EB10 versus host cell EB11.
Figure 2B:
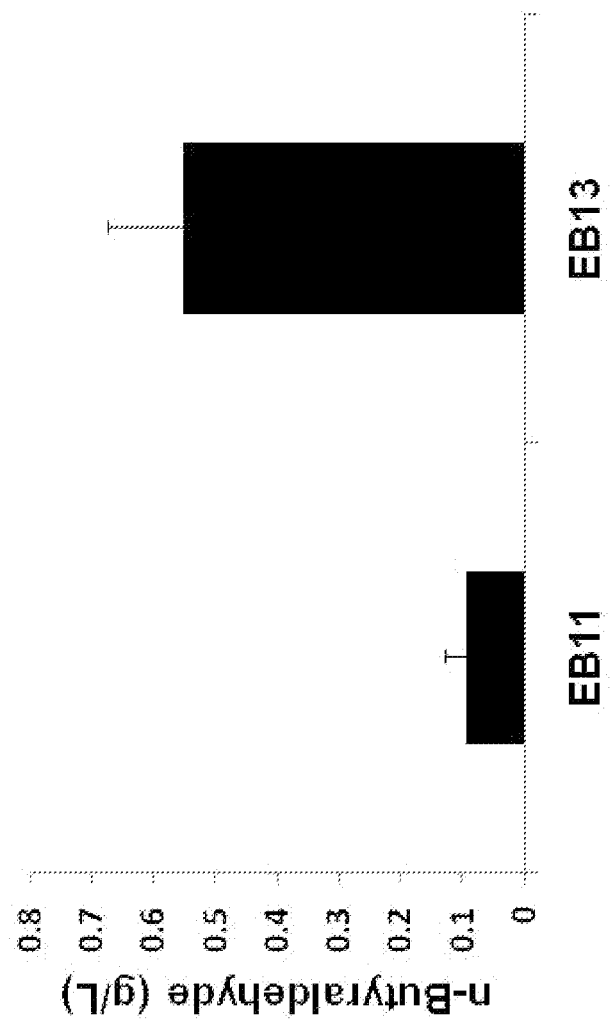
FIG. 2B is an exemplary bar graph depicting results of n-butyraldehyde production (g/L) from glucose by metabolically engineered E. coli strains EB11 versus EB13.

The produced alcohol compounds were quantified by a gas chromatograph equipped with flame ionization detector. The system was a model 7890A gas chromatograph (Agilent Technologies) and a model 7693 autosampler (Agilent Technologies). The separation of alcohol compounds is carried out by A DB-FFAP capillary column (30 m, 0.32-mm internal diameter, 0.25-μm film thickness; Agilent Technologies). GC oven temperature was initially held at 85° C. for 2 min and raised with a gradient of 45° C./min until 235° C. and held for 3 min Helium was used as the carrier gas with 14 p.s.i. inlet pressure. The injector and detector were maintained at 225° C. A 1 μl sample was injected in 25:1 split ratio. 1-Pentanol is used as the internal standard. Exemplary results comparing EB10 with production strain EB11 are shown in FIG. 2A, and the effect of further knock-out mutation in pta in the production strain EB13 (relative to production strain EB11) is shown in FIG. 2B. As is readily apparent, n-butyraldehyde (227 mg/L) could be produced from the broth containing engineered strain EB11 strain, but not in broth containing EB10 alone. Moreover, it is readily apparent that production levels are unexpectedly and significantly increased by deletion of pta (phosphotransacetylase or phosphate acetyltransferase).

Figure 3A:
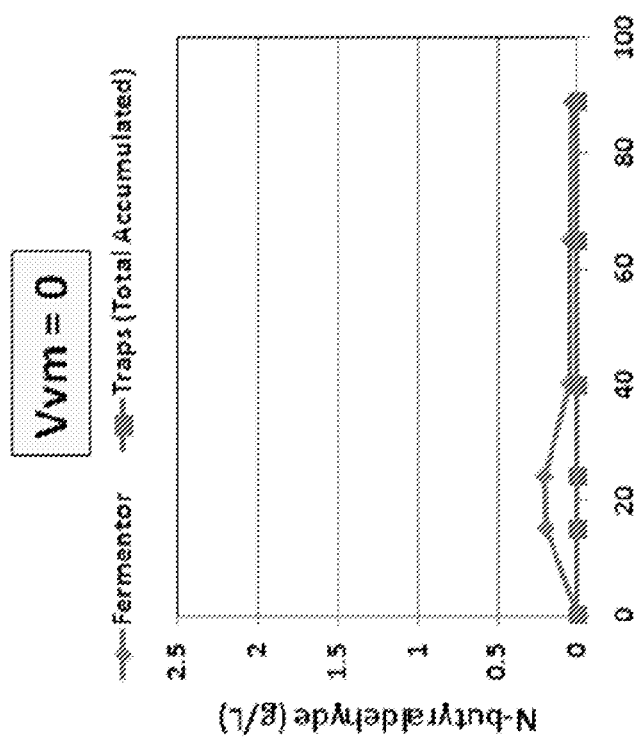
FIGS. 3A-3C are performance graphs showing the concentration of n-butyraldehyde in the fermentor (culture medium) versus time and the cumulative yield of n-butyraldehyde (in the sparging gas) (g/L) versus time (hours) at sparging rates of 0, 1, and 2 vessel volumes per minute (VVM).
Figure 3C:
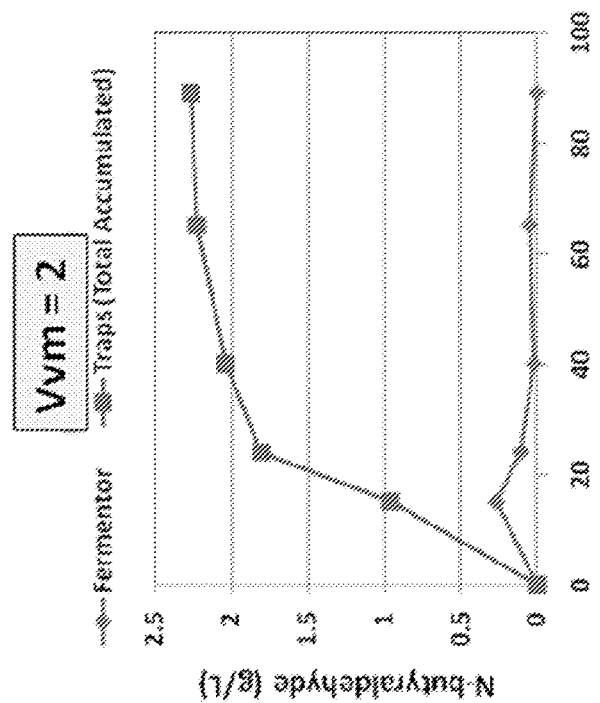
Figure 3B:
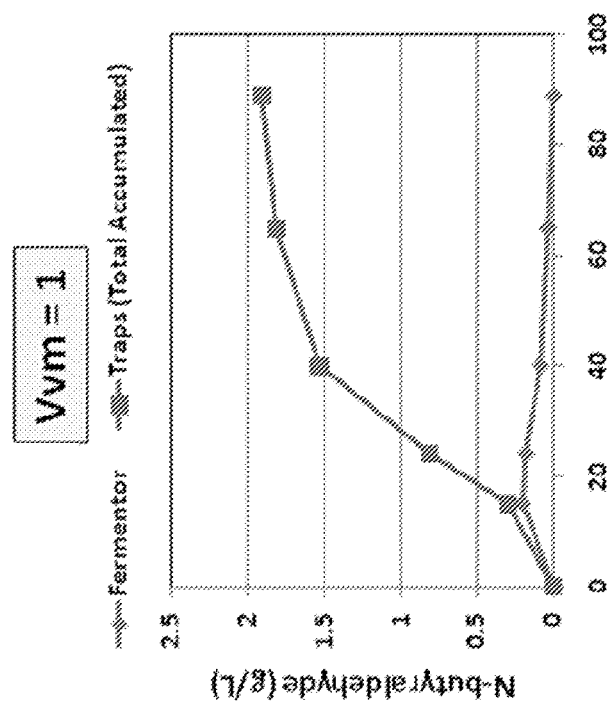

FIGS. 3A-3C show the concentration of n-butyraldehyde produced in the fermentor versus culture time using EB13 and the cumulative yield of n-butyraldehyde versus culture time at sparging rates of 0, 1, and 2 VVM. Referring to FIG. 3A, there is no sparging taking place (0 VVM). The concentration of n-butyraldehyde reaches a maximum of about 0.20-0.25 g/L in the fermentor after about 20 hours, then declines until reaching zero by about 40 hours. In FIGS. 3B-3C, the sparging rates are 1 and 2 VVM, respectively, and the maximum concentration of n-butyraldehyde present in the fermentor is approximately the same as with no sparging, that is, about 0.20-0.25 g/L at or before 20 hours. The results described in the examples and shown in FIG. 2 are consistent with this observation; 0.227 g/L of n-butyraldehyde was recovered after 24 hours culture time.

Referring again to FIGS. 3B-3C, however, the cumulative yield of n-butyraldehyde is significantly increased by sparging during fermentation. At a sparging rate of 1 VVM, for example, the total cumulative yield is greater than the apparent maximum concentration with no sparging. In this example, product is collected with sparging over about 90 hours and the total yield is approximately 1.9 g/L. At a sparging rate of 2 VVM, product is collected over the same amount of time, but with a maximum cumulative yield (MCY) of approximately 2.25 g/L.

This apparent maximum concentration of 0.20-0.25 g/L in the fermentation medium is somewhat surprising. The solubility of n-butyraldehyde in water is approximately 70 g/L, so it could be reasonably expected that the maximum n-butyraldehyde in the fermentor would increase linearly to a substantially higher maximum. Also surprisingly, when an inert gas is sparged through the culture medium, significant amounts of n-butyraldehyde are driven off despite its high solubility. Thus, a desirable high mass yield can be achieved by sparging appropriately. Referring to FIG. 3C in particular, it should be appreciated that half of the maximum cumulative yield ($MCY_{50}$) is acquired at approximately 20 hours, which is around the same time the maximum concentration of n-butyraldehyde is reached in the fermentor. Thus, concurrent sparging at 2 VVM results in approximately five times the product in the same amount of time, and another five times the product collected over approximately the next 70 hours.

Figure 4:
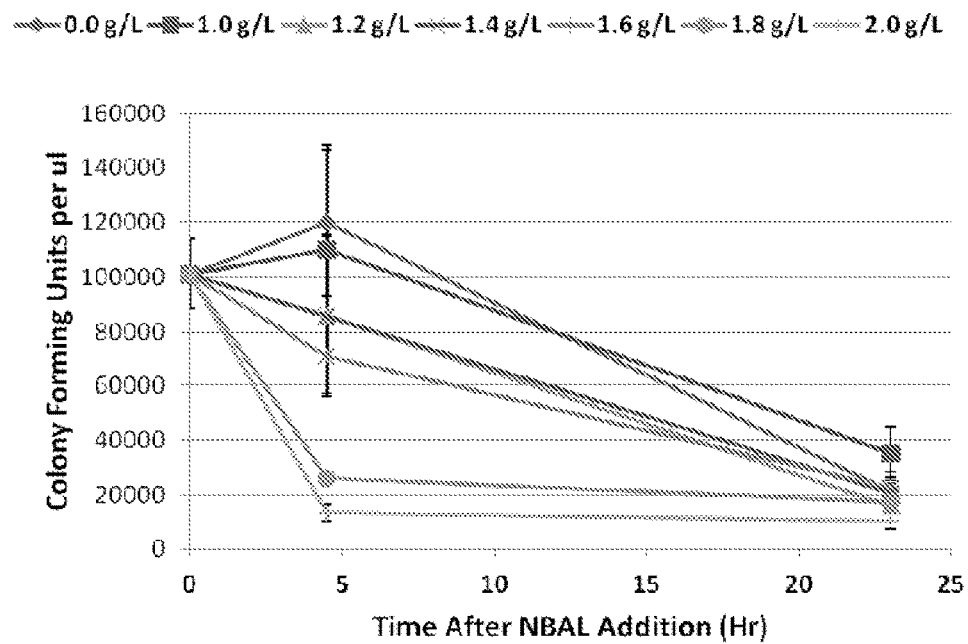
FIG. 4 is a graph illustrating n-butyraldehyde toxicity according to an embodiment of the inventive subject matter, represented as colony forming units per microliter versus time (hours), at various concentrations of n-butyraldehyde.

Turning to FIG. 4, the number of colony forming units per μL of engineered E. coli is shown as a function of time after the addition of various concentrations of n-butyraldehyde (NBAL) is added (incubation test) in a sealed tube to prevent n-butyraldehyde evaporation. In all cases, including the case in which no addition is made, the number of colony forming units tends to a minimum value (e.g., cells no longer viable) after about 24 hours. For a concentration of 1.0 g/L, the graph shows a net increase in colony forming units a little after 5 hours, but concentrations of 1.2 g/L and above show a net decrease even at 4.5 hours. These data suggest that a viability threshold concentration of n-butyraldehyde exists in which there is maximum production of n-butyraldehyde and maximum viability time for the cells. The enhanced yield of n-butyraldehyde achieved using a concurrent sparging method according to the present invention appears to be consistent with the viability analysis.

Figure 5:
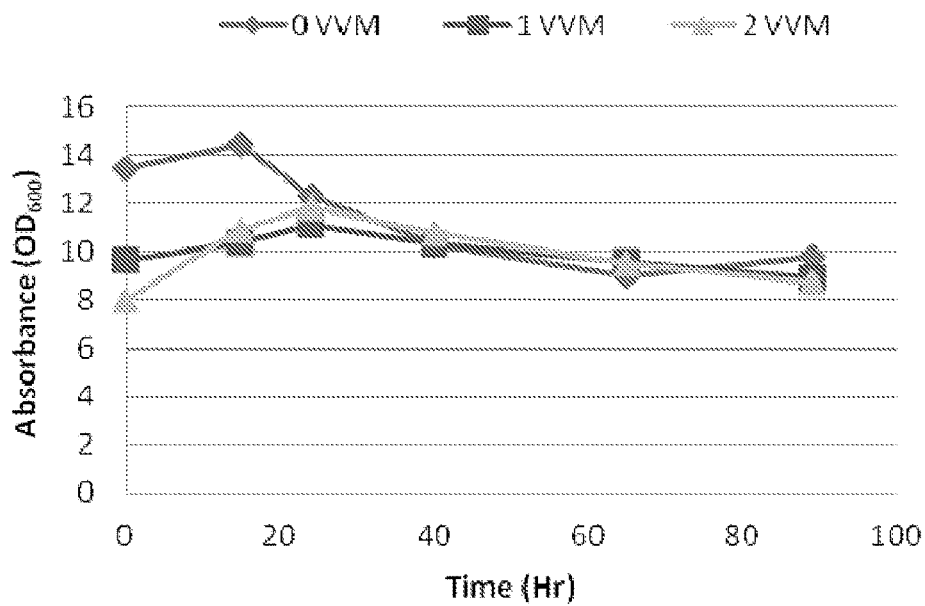
FIG. 5 is a representation of $OD_{600}$ cell density, represented as light absorbance at 600 nanometers, versus time (hours) at sparging rates of 0, 1, and 2 VVM.

FIG. 5 is a representation of $OD_{600}$ cell density, represented as absorbance at 600 nm, versus time (hours) at sparging rates of 0, 1, and 2 VVM. In each case, the data show an increase in cell density at hour 15. At 24 hours, however, the sample sparging at 0 VVM show a marked decrease in cell density, while the samples at 1 and 2 VVM continue to show increases in cell density. At approximately 40 hours, the samples at 1 and 2 VVM continue to show a net increase, and after 89 hours, the sample at 1 VVM shows a net decline, but the sample at 2 VVM continues to show a net increase.

The cell density data appear to be consistent with the viability analysis and the yield data. In particular, the $MCY_{50}$ at 24 hours appears to be consistent with viable cells that are actively producing n-butyraldehyde at a maximum rate. After 24 hours, n-butyraldehyde production continues at a reduced rate until a maximum yield is reached.

Clearly, sparging during the production of n-butyraldehyde provides significantly increased yields of n-butyraldehyde. Without wishing to be bound to any particular method or mechanism, the inventors surmise that the n-butyraldehyde product inhibits its continued production above a minimum yield. This minimum yield, which is approximately equal to the maximum concentration of n-butyraldehyde in the non-sparged system, is significantly lower than what would be expected when considering the solubility of n-butyraldehyde.

With respect to avoiding the inhibition of n-butyraldehyde production, various approaches are therefore contemplated. Because the data appear to show that the MCY increases with increased sparging rates, it would be reasonable to conclude that sparging rates higher than 2 VVM would produce greater increases in the MCY. Thus, sparging rates of at least 2.0 VVM, more typically at least 2.5 VVM, and most typically at least 3.0 VVM are deemed suitable.

Another approach is to recognize that if the n-butyraldehyde product is dissolved in the liquid phase when produced, when sparging occurs, it is the gas-liquid interface where the product may be driven off. If the gas-liquid surface ratio of this interface is increased, an increase in the amount of product driven off may be expected. An increase in the sparging rate (and/or different sparger configuration) would provide smaller bubbles, which would increase the gas-liquid surface ratio. Similarly, increasing the impeller rate would break down gas bubbles, also producing an increased gas-liquid surface ration. Any combination of these methods should produce an increase in the amount of product, its production rate, or both.

Beyond simply modification of the sparging process, the data suggest other potential solutions to increase the MCY of n-butyraldehyde. Regarding microorganisms such as modified E. coli, variations in temperature may affect the production rates. Lowering the temperature in the fermentor would most likely result in more recombinant gene product, albeit at a lower rate. Presumably, there is an optimal sparging rate associated with a given fermentor temperature to achieve maximum yields. Conversely, the temperature could be increased to levels at or near the boiling point of n-butyraldehyde and metabolically engineered microorganisms could be chosen that would grow under these conditions. This would be more like a distillation reaction, in which the n-butyraldehyde would be produced at or near the vapor phase and drive itself out of solution. This could also help maintain a low concentration of product in the fermentor, decreasing potential toxicity effects noted above. Depending on the temperature of the system, sparging at an appropriate rate could also aid in driving off the product.

The system pressure could be varied, with an appropriate sparging protocol. For example, the pressure in the vessel could be decreased, enhancing the release of n-butyraldehyde. The pressure of the sparging gas could be lowered as well, or an intermittent sparging process used, or a combination of these methods to provide an optimal MCY.

These examples utilized a batch fermentation method. One could also envision using a continuous fermentation method instead, in which fresh liquid (culture media) is introduced into the reactor at the same rate that spent media is extracted from the fermentor, while sparging the reactor. In this example, the spent media contains both product and microorganism cells. Product is then collected from the fermentor itself, and the spent media can be sparged again to obtain any residual amounts of product. Consequently, product concentrations could be maintained in the media below a viability threshold concentration.

The fermenter design itself could be modified to provide for collecting the product in a different manner. For example, a thin film fermentor or a hollow fiber fermentor could be employed, giving product in media, which could then be sparged to remove the product. Alternatively, the engineered microorganisms could be immobilized in a gel or alginate-type medium (see e.g., WO2012/004460), and the culture medium could be continuously passed across or through the medium containing the microorganisms and exposed to sparging gas immediately thereafter. This would minimize the exposure of the engineered microorganisms to increased concentrations of product, because the product would continue to flow past the microorganisms with the culture media and be driven off practically immediately. Alternatively, the liquid phase containing the product could be fed into another container that is undergoing the sparging process as the fermentation progresses.

Moreover, it is contemplated that the culture media itself may be augmented with a component that adsorbs n-butyraldehyde, such as molecular sieves, or a water-immiscible partitioning fluid that preferentially dissolves n-butyraldehyde. These would have the effect of removing the n-butyraldehyde from the microorganisms, in accordance with the concept that the removal of n-butyraldehyde from the culture medium would increase its MCY.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of producing n-butyraldehyde, comprising:
   (a) culturing a microorganism in a culture medium with a carbon source, wherein the microorganism is engineered to express at least one heterologous gene to enable in the engineered cell conversion of acetyl-CoA to acetoacetyl-CoA, acetoacetyl-CoA to 3-hydroxybutyryl-CoA, 3-hydroxybutyryl-CoA to crotonyl-CoA, crotonyl-CoA to butyryl-CoA, and butyryl-CoA to n-butyraldehyde and is further engineered by deletion of a butanol dehydrogenase gene and at least one other native alcohol dehydrogenase gene to so allow for increased conversion of the carbon source into n-butyraldehyde;
   (b) recovering the produced n-butyraldehyde from the culture medium by a gas stripping process that maintains dissolved n-butyraldehyde concentrations at or below 1.0 g/L to achieve a cumulative yield of n-butyraldehyde of at least 1.5 g/L;
   wherein the recovering step is performed during the culturing step in which cell density increases while the microorganism produces n-butyraldehyde; and
   (c) reducing n-butyraldehyde to n-butanol in vapor phase; or
   (d) condensing n-butyraldehyde and reducing the n-butyraldehyde to n-butanol in liquid phase.

2. The method of claim 1, wherein the at least one heterologous gene is selected from the group consisting of an acetyl-CoA acetyltransferase, a 3-hydroxyacyl-CoA dehydrogenase, a crotonyl-CoA hydratase, a butyryl-CoA dehydrogenase, a trans-enoyl-CoA reductase, and a butanal dehydrogenase.

3. The method of claim 1, wherein the microorganism is E. coli and is genetically modified to express an artificial operon to allow for expression of atoB, crt, hbd, and bldh.

4. The method of claim 1, wherein the microorganism is E. coli and is genetically modified to have abolished expression of at least one gene selected from the group consisting of ldhA, adhE, frdBC, pta, and yqhD.

5. The method of claim 1, wherein the gas stripping process comprises sparging with a stripping gas at a sparging rate of at least 1 vessel volume per minute, and wherein the culture time is 24 hours or less.

6. The method of claim 1, wherein the recovering step is performed to a cumulative yield of 2.0 g/L at or before 40 hours of culture time.

7. The method of claim 1 wherein the microorganism belongs to a genus selected from the group consisting of Escherichia, Corynebacterium, Clostridium, Zymonomas, Salmonella, Rhodococcus, Pseudomonas, Bacillus, Lactobacillus, Enterococcus, Alcaligenes, Klesiella, Paenibacillus, Arthrobacter, Brevibacterium, Pichia, Candida, Hansenula, Synechococcus, Synechocystis, Anabaena, Ralstonia, Lactococcus and Saccharomyces.

8. The method of claim 1, wherein the microorganism is E. coli.

9. The method of claim 1, wherein n-butyraldehyde is reduced to n-butanol in vapor phase.

10. The method of claim 1, wherein n-butyraldehyde is condensed and reduced to n-butanol in liquid phase.

11. A method of producing n-butyraldehyde, comprising:
    (a) culturing a microorganism in a culture medium with a carbon source, wherein the microorganism is engineered to express at least one heterologous gene to enable in the engineered cell conversion of acetyl-CoA to acetoacetyl-CoA, acetoacetyl-CoA to 3-hydroxybutyryl-CoA, 3-hydroxybutyryl-CoA to crotonyl-CoA, crotonyl-CoA to butyryl-CoA, and butyryl-CoA to n-butyraldehyde and is further engineered by deletion of a butanol dehydrogenase gene and at least one other native alcohol dehydrogenase gene to so allow for increased conversion of the carbon source into n-butyraldehyde; and
    (b) recovering the produced n-butyraldehyde from the culture medium by a gas stripping process that maintains dissolved n-butyraldehyde concentrations at or below 1.0 g/L and comprises a step of sparging under conditions effective to provide 50% of a maximum cumulative yield ($MCY_{50}$) at or before 24 hours culture time;
    wherein the recovering step is performed during the culturing step in which cell density increases while the microorganism produces n-butyraldehyde; and
    (c) reducing n-butyraldehyde to n-butanol in vapor phase; or
    (d) condensing n-butyraldehyde and reducing the n-butyraldehyde to n-butanol in liquid phase.

12. The method of claim 11, wherein the culturing step comprises culturing in a batch culture over at least 18 hours.

13. The method of claim 11, wherein the $MCY_{50}$ is recovered in 20 hours or less.

14. The method of claim 13, wherein the $MCY_{50}$ is at least 1 g/L.

15. A method of producing n-butyraldehyde, comprising:
    (a) culturing a microorganism in a culture medium with a carbon source, wherein the microorganism is engineered to express at least one heterologous gene to enable in the engineered cell conversion of acetyl-CoA to acetoacetyl-CoA, acetoacetyl-CoA to 3-hydroxybutyryl-CoA, 3-hydroxybutyryl-CoA to crotonyl-CoA, crotonyl-CoA to butyryl-CoA, and butyryl-CoA to n-butyraldehyde and is further engineered by deletion of a butanol dehydrogenase gene and at least one other native alcohol dehydrogenase gene to so allow for increased conversion of the carbon source into n-butyraldehyde;

(b) recovering the produced n-butyraldehyde from the culture medium by a gas stripping process at a sparging rate effective to maintain dissolved n-butyraldehyde at a concentration at or below 1.0 g/L;

wherein the recovering step is performed during the culturing step in which cell density increases while the microorganism produces n-butyraldehyde; and (c) reducing n-butyraldehyde to n-butanol in vapor phase; or (d) condensing n-butyraldehyde and reducing the n-butyraldehyde to n-butanol in liquid phase.

16. The method of claim 15, wherein the gas stripping process uses continuous sparging.

17. The method of claim 16, wherein the continuous sparging is at a sparging rate of at least 1 vessel volume per minute.

18. A method of producing n-butyraldehyde, comprising:

(a) culturing a microorganism with a carbon source, wherein the microorganism is engineered to express at least one heterologous gene to enable in the engineered cell conversion of acetyl-CoA to acetoacetyl-CoA, acetoacetyl-CoA to 3-hydroxybutyryl-CoA, 3-hydroxybutyryl-CoA to crotonyl-CoA, crotonyl-CoA to butyryl-CoA, and butyryl-CoA to n-butyraldehyde and is further engineered by deletion of a butanol dehydrogenase gene and at least one other native alcohol dehydrogenase gene to so allow for increased conversion of the carbon source into n-butyraldehyde; and (b) recovering the produced n-butyraldehyde from culture broth by a gas stripping process that maintains dissolved n-butyraldehyde concentrations at or below 1.0 g/L to prevent a net decline of cell density for up to at least 40 hours;

wherein the recovering step is performed during the culturing step in which cell density increases while the microorganism produces n-butyraldehyde; and (c) reducing n-butyraldehyde to n-butanol in vapor phase; or (d) condensing n-butyraldehyde and reducing the n-butyraldehyde to n-butanol in liquid phase.

19. The method of claim 18, wherein the gas stripping process is effective to produce a net increase in cell density over at least 24 hours.

* * * * *